US009829413B2

(12) United States Patent
Marek et al.

(10) Patent No.: US 9,829,413 B2
(45) Date of Patent: Nov. 28, 2017

(54) EMISSIONS MEASUREMENT EQUIPMENT AND METHOD

(71) Applicant: AVL TEST SYSTEMS, INC., Plymouth, MI (US)

(72) Inventors: Gerald Marek, Pinckney, MI (US); Ali Ganjidoost, Dearborn, MI (US); Colin Chisholm, South Lyon, MI (US)

(73) Assignee: AVL TEST SYSTEMS, INC., Plymouth, MI (US)

( * ) Notice: Subject to any disclaimer, the term of this patent is extended or adjusted under 35 U.S.C. 154(b) by 250 days.

(21) Appl. No.: 14/410,417

(22) PCT Filed: Jun. 25, 2013

(86) PCT No.: PCT/US2013/047578
§ 371 (c)(1),
(2) Date: Dec. 22, 2014

(87) PCT Pub. No.: WO2014/008040
PCT Pub. Date: Jan. 9, 2014

(65) Prior Publication Data
US 2015/0338311 A1 Nov. 26, 2015

Related U.S. Application Data

(60) Provisional application No. 61/663,966, filed on Jun. 25, 2012.

(51) Int. Cl.
*G01M 15/10* (2006.01)
*G01N 1/22* (2006.01)

(52) U.S. Cl.
CPC ........ *G01M 15/102* (2013.01); *G01N 1/2202* (2013.01); *G01N 1/2247* (2013.01); *G01N 1/2252* (2013.01)

(58) Field of Classification Search
None
See application file for complete search history.

(56) References Cited

U.S. PATENT DOCUMENTS 5,468,968 A * 11/1995 Bailey ........................ G01T 7/04
250/304
5,551,311 A * 9/1996 Ogden ...................... G01N 1/24
422/119

(Continued)

FOREIGN PATENT DOCUMENTS

WO 2006/091095 A2 8/2006

OTHER PUBLICATIONS

International Search Report and Written Opinion for PCT/US2013/047578, dated Nov. 25, 2013; ISA/KR.

(Continued)

*Primary Examiner* — Paul West
*Assistant Examiner* — Xin Zhong
(74) *Attorney, Agent, or Firm* — Harness, Dickey & Pierce, P.L.C.

(57) ABSTRACT

An emissions test apparatus is provided and may include a filter housing having at least one of a first RFID tag and a first bar code identifying the filter housing. A filter media may be selectively disposed within the filter housing and may include at least one of a second RFID tag and a second bar code identifying the filter media. A controller may link the filter housing and the filter media when the filter media is disposed within the filter housing based on information provided by the at least one of the first RFID tag and the first bar code and the at least one of the second RFID tag and the second bar code.

21 Claims, 10 Drawing Sheets

(56) References Cited

U.S. PATENT DOCUMENTS

| | | | |
|---|---|---|---|
| 5,591,974 | A | 1/1997 | Troyer et al. |
| 5,635,403 | A * | 6/1997 | Bailey ........................ G01T 7/04 |
| | | | 422/403 |
| 5,717,147 | A | 2/1998 | Basch et al. |
| 7,299,710 | B2 | 11/2007 | Syage |
| 2004/0069046 | A1 | 4/2004 | Sunshine et al. |
| 2004/0083826 | A1 | 5/2004 | Botha et al. |
| 2005/0247105 | A1* | 11/2005 | Dikken .............. B01D 39/1692 |
| | | | 73/28.04 |
| 2007/0036683 | A1 | 2/2007 | Hirst |
| 2009/0223310 | A1 | 9/2009 | Syage et al. |
| 2010/0218595 | A1 | 9/2010 | Dikken et al. |
| 2014/0286836 | A1* | 9/2014 | Clavaguera .......... G01N 1/2205 |
| | | | 422/535 |

OTHER PUBLICATIONS

European Search Report for PCT/US2013/047578, dated Jan. 25, 2016.

* cited by examiner

EMISSIONS MEASUREMENT EQUIPMENT AND METHOD

CROSS-REFERENCE TO RELATED APPLICATIONS

This application claims the benefit of U.S. Provisional Application No. 61/663,966, filed on Jun. 25, 2012. The entire disclosure of the above application is incorporated herein by reference.

FIELD

The present disclosure relates to emissions measurement equipment and more particularly to a method of operating emissions measurement equipment that improves the accuracy and integrity of test results produced by the emissions measurement equipment.

BACKGROUND

This section provides background information related to the present disclosure which is not necessarily prior art.

Internal combustion engines are used in a wide variety of applications to provide a motive force to large and small-duty vehicles alike. The motive force applied to the particular vehicle is achieved by the combustion of a fuel with an oxidizer in a combustion chamber of the engine. The combustion of the fuel/oxidizer mixture within the combustion chamber causes the temperature and pressure within the combustion chamber to be elevated, thereby driving an element of the engine (i.e., a piston and crankshaft of an automobile) to propel the vehicle forward.

While combustion of the fuel/oxidizer within the combustion chamber provides adequate power to drive a vehicle, the combustion process results in an exhaust gas, which is typically discharged into the atmosphere via an exhaust pipe of the vehicle. Such exhaust gas typically includes particulate matter, which is formed when the exhaust from the engine mixes with ambient air. Specifically, when the exhaust gas mixes with ambient air, the combustion products present in the exhaust gas (i.e., soot, hydrocarbons, sulfates, nitrates, and ash) form via the physio-chemical processes of adsorption, condensation, and agglomeration into particles of various sizes.

The emission of particulates from exhaust gases of internal combustion engines such as diesel engines and gasoline direct-injection engines are restricted by various regulatory bodies both in the United States and abroad. The regulatory bodies responsible for controlling emissions from internal combustion engines promulgate various measurement methodologies and criteria to test exhaust gas and the resultant particulate matter therein. One such measurement methodology includes mixing and diluting a sample of exhaust gas with ambient air under controlled conditions. The flow of exhaust gas and air is passed through a particulate filter, which is subsequently analyzed to determine the weight of the particulate matter collected by the filter.

While collecting particulate matter on a filter from an exhaust gas/air mixture provides an accurate methodology for determining the amount of particulate matter contained within the exhaust gas, the integrity of such measurements is often compromised if the filters do not properly correspond to a particular test flow. For example, an emissions measurement test apparatus may include three phases, as required by Federal Test Procedure 75 (FTP-75), and, as a result, may likewise include three fluid test streams respectively associated with three filter media. Properly assigning each filter media to the particular phase prior to, during, and after the emissions test is essential to ensure the gravimetric data of each filter media is properly attributed to the particular phase.

If the filter media are not properly assigned to the various phases of the emissions test, the resulting data and, thus, the reported emissions for the engine, may be inaccurate. Inaccurate test results may result in the engine failing the particular standard and, thus, failing to meet certification. Accordingly, care must be taken when performing an emissions test to ensure that each filter media inserted into and removed from an emissions test apparatus is properly assigned to a particular phase of an emissions test prior to and following performance of the test to ensure accurate and reliable results.

SUMMARY

This section provides a general summary of the disclosure, and is not a comprehensive disclosure of its full scope or all of its features.

An emissions test apparatus is provided and may include a filter housing having at least one of a first RFID tag and a first bar code identifying the filter housing. A filter media may be selectively disposed within the filter housing and may include at least one of a second RFID tag and a second bar code identifying the filter media. A controller may link the filter housing and the filter media when the filter media is disposed within the filter housing based on information provided by the at least one of the first RFID tag and the first bar code and the at least one of the second RFID tag and the second bar code.

In another configuration, an emissions test apparatus is provided and may include a filter housing and a filter media selectively disposed within the filter housing. The filter media may include an RFID tag identifying the filter media. A controller may link the filter housing and the filter media when the filter media is disposed within the filter housing based on information provided by the RFID tag.

In another configuration, an emissions test apparatus is provided and may include a filter carrier and a filter media selectively disposed within the filter carrier. The filter media may include an RFID tag identifying the filter media. A controller may link the filter carrier and the filter media when the filter media is disposed within the filter carrier based on information provided by the RFID tag.

In another configuration, an emissions test apparatus is provided and may include a filter carrier having at least one of a first RFID tag and a first bar code identifying the filter housing. A filter media may be selectively disposed within the filter carrier and may include at least one of a second RFID tag and a second bar code identifying the filter media. A controller may link the filter carrier and the filter media when the filter media is disposed within the filter carrier based on information provided by the at least one of the first RFID tag and the first bar code and the at least one of the second RFID tag and the second bar code.

A method is provided and may include identifying a filter housing of an emissions test apparatus and identifying a filter media disposed within the filter housing. The method may further include linking by a controller the filter media to the filter housing, installing the filter housing in a test fixture of the emissions test apparatus, and identifying the filter housing following the installation of the filter housing into the test fixture. The method may further include identifying the test fixture and linking by the controller the filter housing to the test fixture.

In another configuration, a method is provided and may include determining by a controller whether a filter housing is installed in a test fixture of an emissions test apparatus. The method may further include identifying the filter housing, identifying the test fixture, and linking by the controller the filter housing to the test fixture following the determination as to whether the filter housing is installed in the test fixture. The method may further include preventing by the controller linking of the filter housing to the test fixture if the filter housing is not installed in the test fixture.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
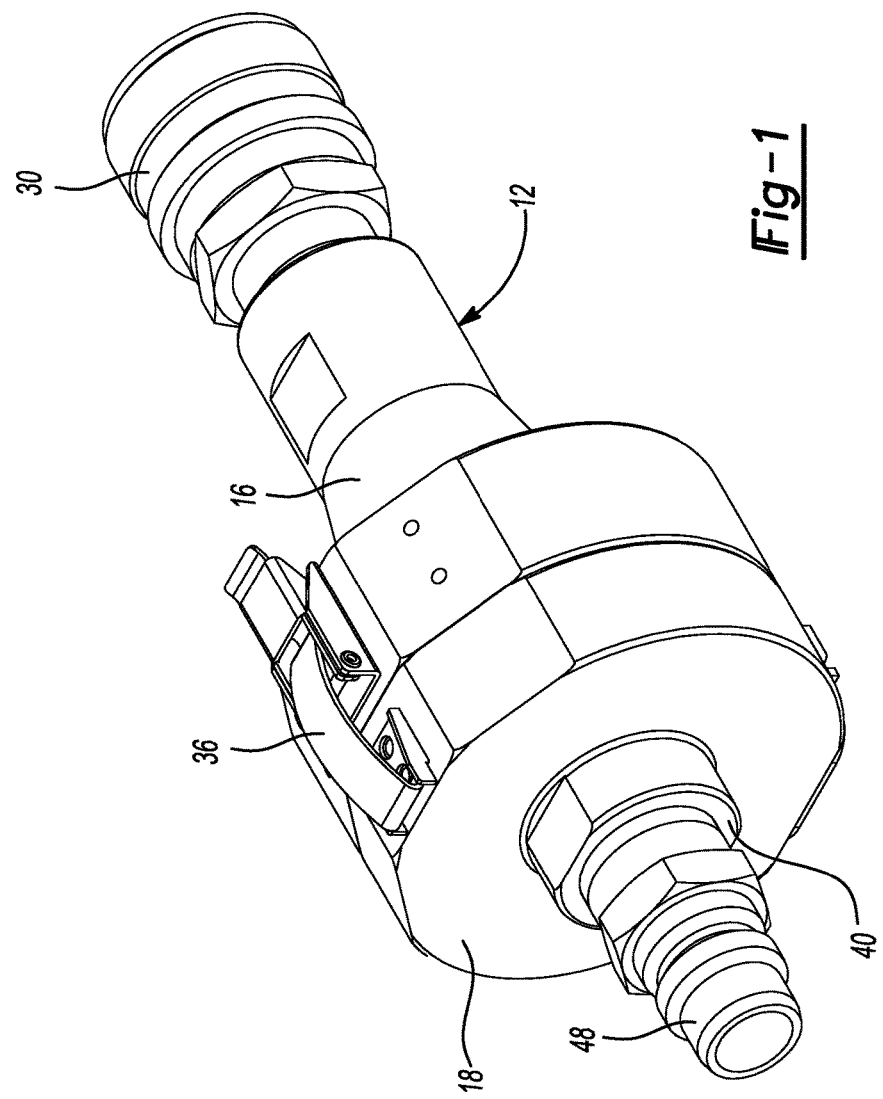
FIG. 1 is a perspective view of a filter housing in accordance with the principles of the present disclosure.
Figure 2:
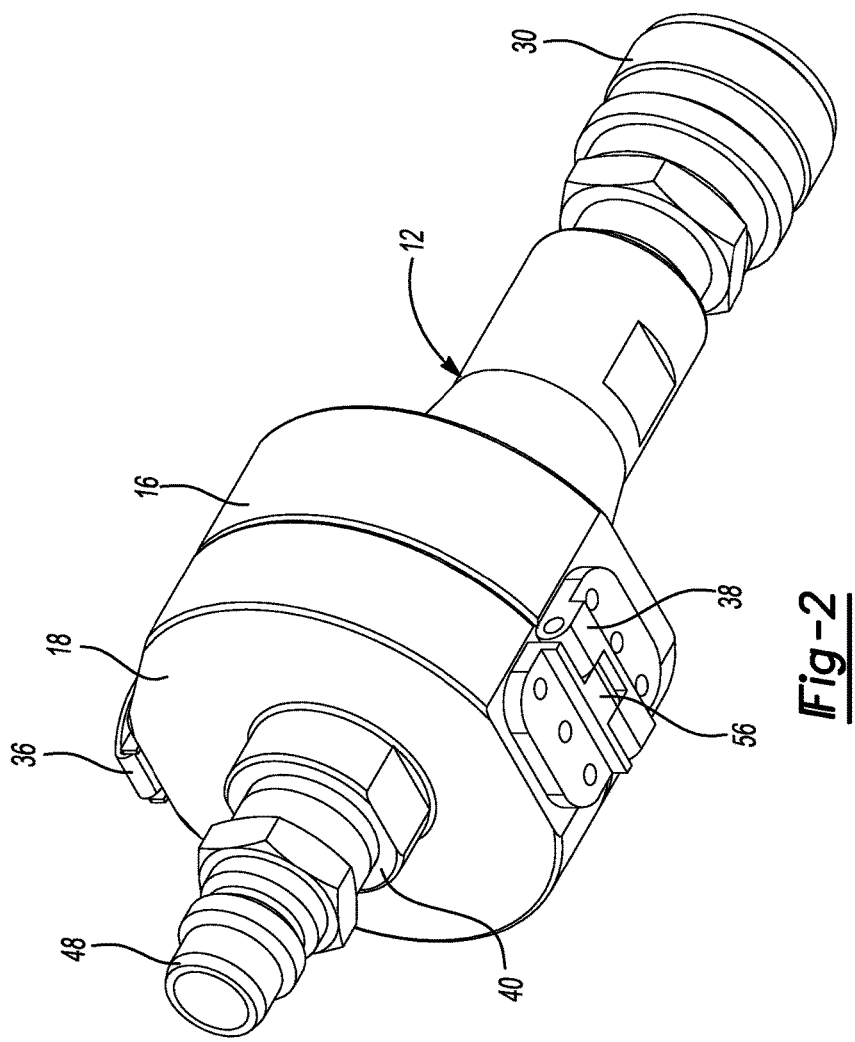
FIG. 2 is a perspective view of a filter housing in accordance with the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to the figures, an emissions test apparatus 10 (FIG. 7) is provided and may include a filter housing 12 and a filter media 14. The filter media 14 may be selectively disposed within the filter housing 12 and may cooperate with the filter housing 12 during an emissions test to trap particulate matter contained within an airstream containing exhaust gas and ambient air.

Figure 6:
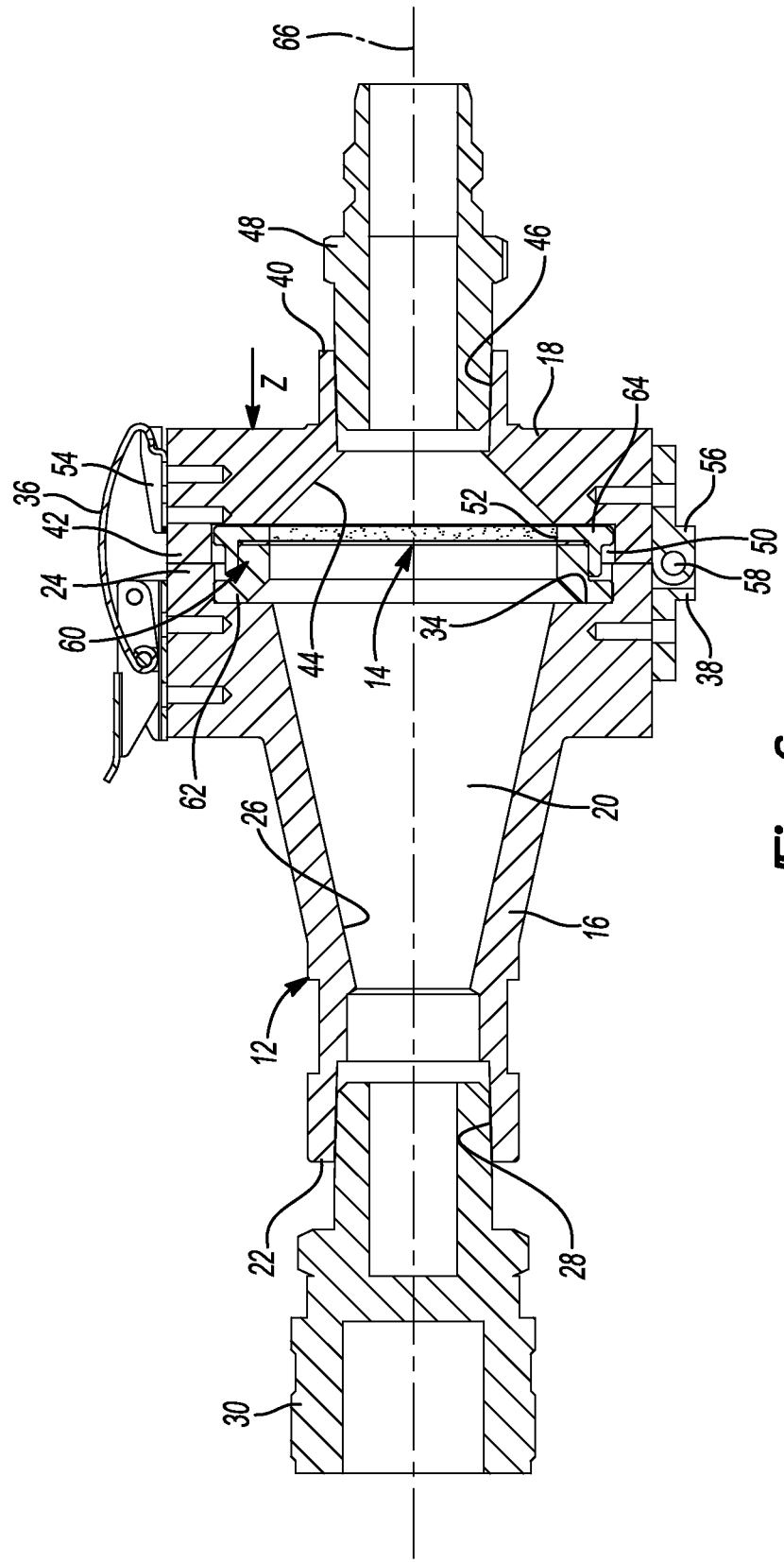
FIG. 6 is a cross-sectional view of the filter housing of FIG. 1 taken along line 6-6 of FIG. 5.

The filter housing 12 may include a first housing 16 and a second housing 18 that cooperate to form an inner volume 20 (FIG. 6) of the filter housing 12. The first housing 16 may include a first end 22, a second end 24, and a tapered bore 26 extending between the first end 22 and the second end 24. The first end 22 may include a substantially cylindrical port 28 that receives a fitting 30 therein. The second end 24 is disposed on an opposite end of the first housing 16 from the first end 22 and may include a recess 32 that defines a support surface 34. The recess 32 and the support surface 34 may cooperate to support the filter media 14 within the first housing 16 to properly position the filter media 14 within the inner volume 20 of the filter housing 12. The first housing 16 may additionally include a latch mechanism 36 and a hinge 38 formed on an opposite side of the first housing 16 than the latch mechanism 36.

The second housing 18 may be pivotably attached to the first housing 16 and may include a first end 40, a second end 42, and a tapered bore 44 extending between the first end 40 and the second end 42. The first end 40 may include a port 46 (FIG. 6) that receives a fitting 48 therein. As with the fitting 30 of the first end 22, the fitting 48 is likewise in fluid communication with the tapered bore 44 of the second housing 18. The second end 42 is formed on an opposite end of the second housing 18 from the first end 40 and may include a recess 50 having a support surface 52 that cooperates with the recess 32 and the support surface 34 of the first housing 16 to properly position and support the filter media 14 within the filter housing 12.

The second housing 18 may additionally include a retention element 54 and a hinge 56 formed on an opposite side of the second housing 18 than the retention element 54. The retention element 54 may selectively cooperate with the latch mechanism 36 to fix a relative position between the first housing 16 and the second housing 18. The hinge 56 may cooperate with the hinge 38 of the first housing 16 to allow the first housing 16 and the second housing 18 to pivot relative to one another about the hinges 38, 56. Specifically, a pin 58 (FIG. 6) may be inserted into and through the hinges 38, 56 of the first housing 16 and the second housing 18, respectively, to allow the first housing 16 and the second housing 18 to be pivotably connected to one another about the pin 58.

The filter media 14 may be formed from virtually any material that permits air to flow through the filter media 14 while concurrently trapping particulate matter associated with an fluid stream containing exhaust gas from an engine. The filter media 14 may be supported within the filter housing 12 by a filter carrier or "puck" 60 having a first housing 62 and a second housing 64. The filter media 14 may be positioned between the first housing 62 and the second housing 64 and may be held in place when the first housing 62 is inserted into the second housing 64. Specifically, the first housing 62 may be press-fit into the second housing 64 with the filter media 14 disposed therebetween. Interaction between the first housing 62 and the second housing 64 may fix the filter media 14 for movement with the first housing 62 and the second housing 64 when the first housing 62 is press-fit into the second housing 64.

In operation, when the first housing 16 is pivotably attached to the second housing 18 at the hinges 38, 56, the filter media 14 may be positioned within the recesses 32, 50 of the first housing 16 and the second housing 18, respectively. As such, the first housing 62 and the second housing 64 of the filter carrier 60 may be in an abutting relationship with the support surfaces 34, 52 of the first housing 16 and the second housing 18, respectively.

The filter media 14 may be held within the filter housing 12 in a desired position such that the first housing 62 is in an abutting relationship with the support surface 34 and the second housing 64 is in an abutting relationship with the support surface 52 when the latch mechanism 36 engages the retention element 54 to fix a position of the first housing 16 relative to the second housing 18. For example, when the latch mechanism 36 engages the retention element 54, a force may be applied to the second housing 18 in the "Z" direction (FIG. 6) to clamp the filter media 14 between the first housing 16 and the second housing 18. The force applied to the filter media 14 is maintained until the latch mechanism 36 is moved from the latched state (FIG. 6) to the unlatched state (not shown) to once again permit pivotal movement of the second housing 18 relative to the first housing 16.

When the latch mechanism 36 is in the latched state such that the second end 24 of the first housing 16 is in an abutting relationship with the second end 42 of the second housing 18, the first housing 16 is fluidly coupled to the second housing 18. As such, the fitting 30 associated with the first housing 16 is fluidly coupled to the fitting 48 associated with the second housing 18 such that the first housing 16, the second housing 18, the fitting 30, and the fitting 48 are fluidly coupled to one another along a longitudinal axis 66 of the filter housing 12.

Figure 7:
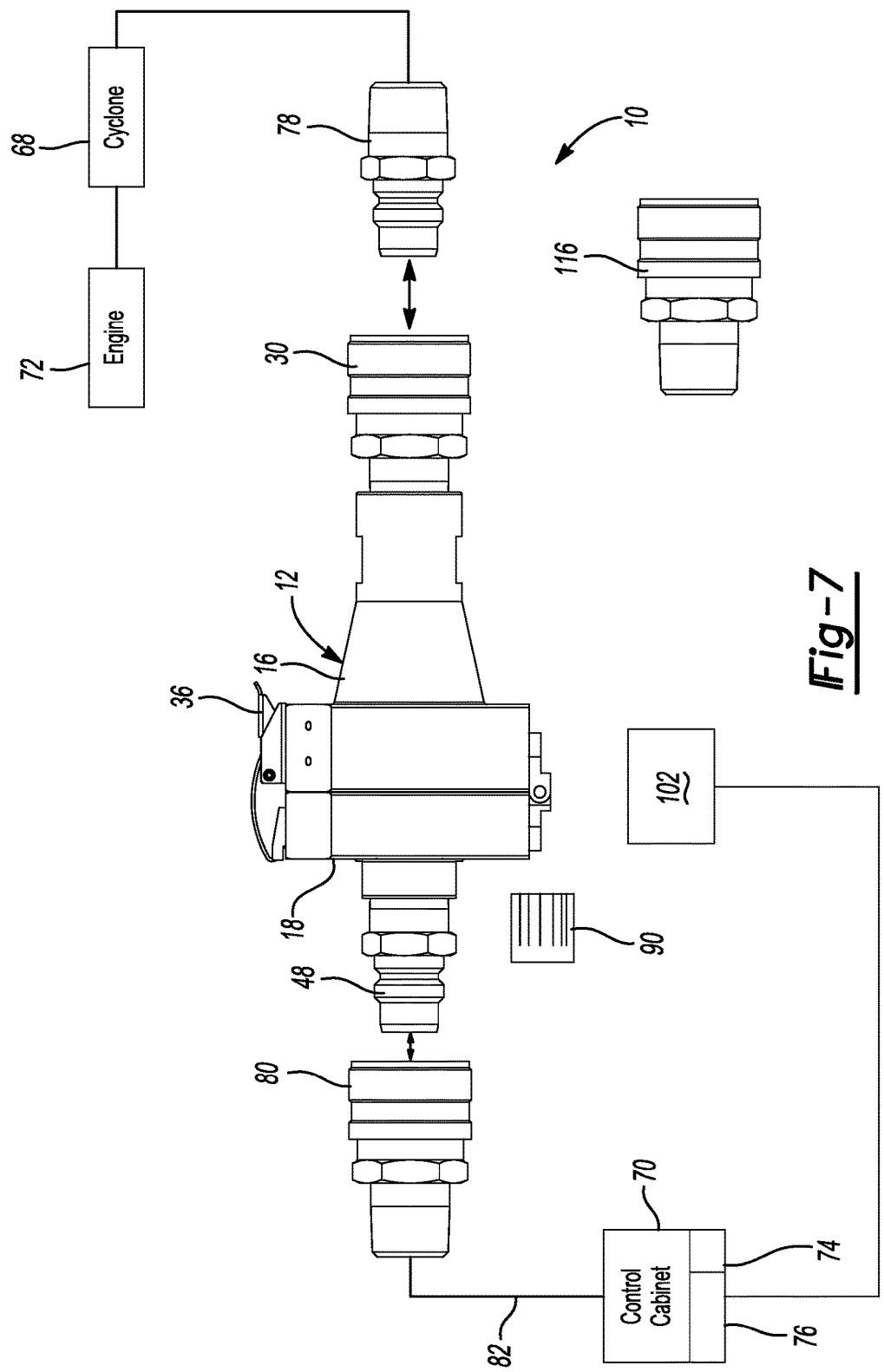
FIG. 7 is a partial exploded view of an emissions test apparatus in accordance with the principles of the present disclosure and incorporating the filter housing of FIG. 1.

With particular reference to FIG. 7, the emissions test apparatus 10 is shown to include a cyclone 68 and a control cabinet 70. The cyclone 68 may be attached to an internal combustion engine 72 to test the emissions of the engine 72. The cyclone 68 may receive exhaust gas from the engine 72 and may mix the exhaust gas with ambient air in an effort to dilute the exhaust gas prior to testing. The cyclone 68 may produce one or more fluid streams and may direct each fluid stream to a respective filter housing 12. In one configuration, the cyclone 68 creates three fluid streams to test the engine 72 in three phases; a cold-start phase, a transient phase, and a hot-start phase in accordance with FTP-75. If the cyclone 68 generates three fluid streams to generate the foregoing phases, each fluid stream would include a filter housing 12 having a filter media 14 disposed therein.

The control cabinet 70 may include a vacuum 74 that draws the exhaust gas/ambient air mixture from the cyclone 68 through the filter housing 12 when the filter housing 12 is attached to the cyclone 68 and the control cabinet 70. The control cabinet 70 may additionally include a controller 76 that controls operation of the cyclone 68 and/or vacuum 74.

In operation, the filter housing 12 may be attached to the cyclone 68 and to the control cabinet 70 at the fittings 30, 48. Specifically, the fittings 30, 48 associated with the first housing 16 and the second housing 18, respectively, may be quick-connect fittings that allow the filter housing 12 to be quickly connected and disconnected from the cyclone 68 and the control cabinet 70. As such, the cyclone 68 may include a fitting 78 that is selectively connected to the fitting 30 of the first housing 16 and the control cabinet 70 may include a fitting 80 that is selectively connected to the fitting 48 of the second housing 18 to allow the filter housing 12 to be easily and quickly connected to the cyclone 68 and to the control cabinet 70.

In one configuration, the fitting 80 associated with the control cabinet 70 may include a flexible, fluid line 82 that allows the fitting 80 to be movable relative to the filter housing 12 to facilitate attachment of the filter housing 12 to the fitting 78 of the cyclone 68 and to the fitting 80 of the control cabinet 70. Once the fitting 30 of the first housing 16 is connected to the fitting 78 and the fitting 48 of the second housing 18 is connected to the fitting 80, the cyclone 68 is fluidly coupled to the vacuum 74 of the control cabinet 70 via the filter housing 12.

A test may be performed by starting the internal combustion engine 72 to produce an exhaust gas. The exhaust gas is received by the cyclone 68, which mixes the exhaust gas with ambient air to dilute the gas prior to reaching the fitting 78. The exhaust gas/ambient air mixture is drawn through the filter housing 12 due to the force imparted on the exhaust gas/ambient air mixture by the vacuum 74 associated with the control cabinet 70. The exhaust gas/ambient air mixture is drawn into the inner volume 20 of the filter housing 12 and passes through the filter media 14. Specifically, the exhaust gas/ambient air mixture is forced toward the filter media 14 due to the shape of the tapered bore 26 of the first housing 16 and is likewise directed to the fitting 48 by the tapered bore 44 after the exhaust gas/ambient air mixture passes through the filter media 14.

The exhaust gas/ambient air mixture exits the filter housing 12 at the fitting 48 and enters the control cabinet 70 via the fluid line 82. Once a predetermined volume of exhaust gas/ambient air mixture passes through the filter media 14, the engine 72 is stopped and the filter housing 12 may be disconnected from the fittings 78, 80. At this point, the latch mechanism 36 is moved into the unlatched state to allow pivotal movement between the first housing 16 and the second housing 18 to allow removal of the filter carrier 60 and, thus, the filter media 14, from the filter housing 12.

The filter media 14 may be removed from the first housing 62 and the second housing 64 of the filter carrier 60 to allow the filter media 14 to be weighed. The weight of the filter media 14 is compared to a pre-test weight of the filter media 14 to determine the weight of particulate matter collected by the filter media 14 during the emissions test. The weight of the filter media 14 is compared to the weight of the filter media 14 prior to the exhaust gas/ambient air mixture flowing through the filter media 14 during the emissions test to determine the weight of particulate matter collected by the filter media 14 and, thus, the amount of particulate matter created by operation of the internal combustion engine 72. The weight of the filter media 14 and the particular phase of the emissions test is recorded for use in determining the overall emissions of the internal combustion engine 72.

As thus far described, the filter media 14 may be used in conjunction with the filter housing 12 to determine the emissions of the internal combustion engine 72 for a particular phase of an emissions test. Further, several filter housings 12, each containing a filter media 14, may be used to test three fluid streams, for example, to determine compliance of the internal combustion engine with FTP-75. In so doing, the filter media 14 assigned to each particular filter housing 12 and each fluid stream must be recorded to obtain an accurate measurement of each phase. Namely, each filter media 14 and, thus, the resulting particulate matter collected by the filter media 14, must be properly assigned to a particular filter housing 12 and to a particular fluid stream to allow the weight of the particulate matter to be properly attributed to a particular phase of the FTP-75 measurement standard.

The emissions test apparatus 10 may include an identification system that allows the filter media 14 to be properly assigned and linked to a particular filter housing 12 and, further, to allow a particular filter housing 12 to be properly assigned and linked to a particular air flow. In one configuration, the filter media 14 may include a bar code 84 (FIG. 3) that identifies the filter media 14 and assigns the filter media 14 with a specific identifier. Likewise, one of the first housing 16 and the second housing 18 of the filter housing 12 may include a first bar code 86 disposed proximate to the recess 32 and a second bar code 88 located externally from the inner volume 20 of the filter housing 12. Each of the bar codes 86, 88 identifies the first housing 16 and, thus, the particular filter housing 12, and assigns the filter housing 12 with a specific identifier.

The filter carrier 60 may also include one or more bar codes 85 to identify the particular filter carrier 60 and assign the filter carrier 60 with a specific identifier. In one configuration, the filter carrier 60 includes two bar codes 85 (FIG. 3) that are positioned at different locations and at different angles relative to one another. Positioning the bar codes 85 at different locations and/or at different locations facilitates reading of the bar codes 85.

Finally, each fluid stream of the emissions test apparatus 10 may also include a bar code 90 (FIG. 7) that identifies each fluid stream. For example, if the emissions test apparatus 10 is configured to test three separate fluid streams by utilizing three different test fixtures, each having a fitting 78 coupled to the cyclone 68 and a fitting 80 connected to the vacuum 74 of the control cabinet 70, each fluid stream may be assigned a bar code 90 located on the particular test fixture to assign each air flow an identifier to differentiate amongst the various test fixtures and associated fluid streams and phases. The bar code 90 may be located on the test fixture proximate to the filter housing 12 such that the bar code 90 is located proximate to the bar code 88 located on an external surface of the first housing 16 of the filter housing 12.

While the filter media 14, the filter housing 12, the filter carrier 60, and the fluid streams of the test apparatus 10 are described as including bar codes 84, 85, 86, 88, 90, respectively, other forms of identification may be used to assign each of the filter media 14, the filter housing 12, the filter carrier 60, and the fluid streams of the test apparatus 10 a specific identifier. Namely, radio-frequency identification (RFID) may be used to identify any one of or each of the filter housing 12, the filter media 14, the filter carrier 60, and the fluid streams in addition to or in place of the bar codes 84, 85, 86, 88, 90. For example, the filter media 14 may be provided with an RFID tag 100 (FIG. 3) in place of or in addition to the bar code 84. The RFID tag 100 may be read by an RFID reader 102 (FIG. 7) associated with the test apparatus 10 that may identify the particular filter media 14 to the controller 76 via wired or wireless communication.

Figure 8:
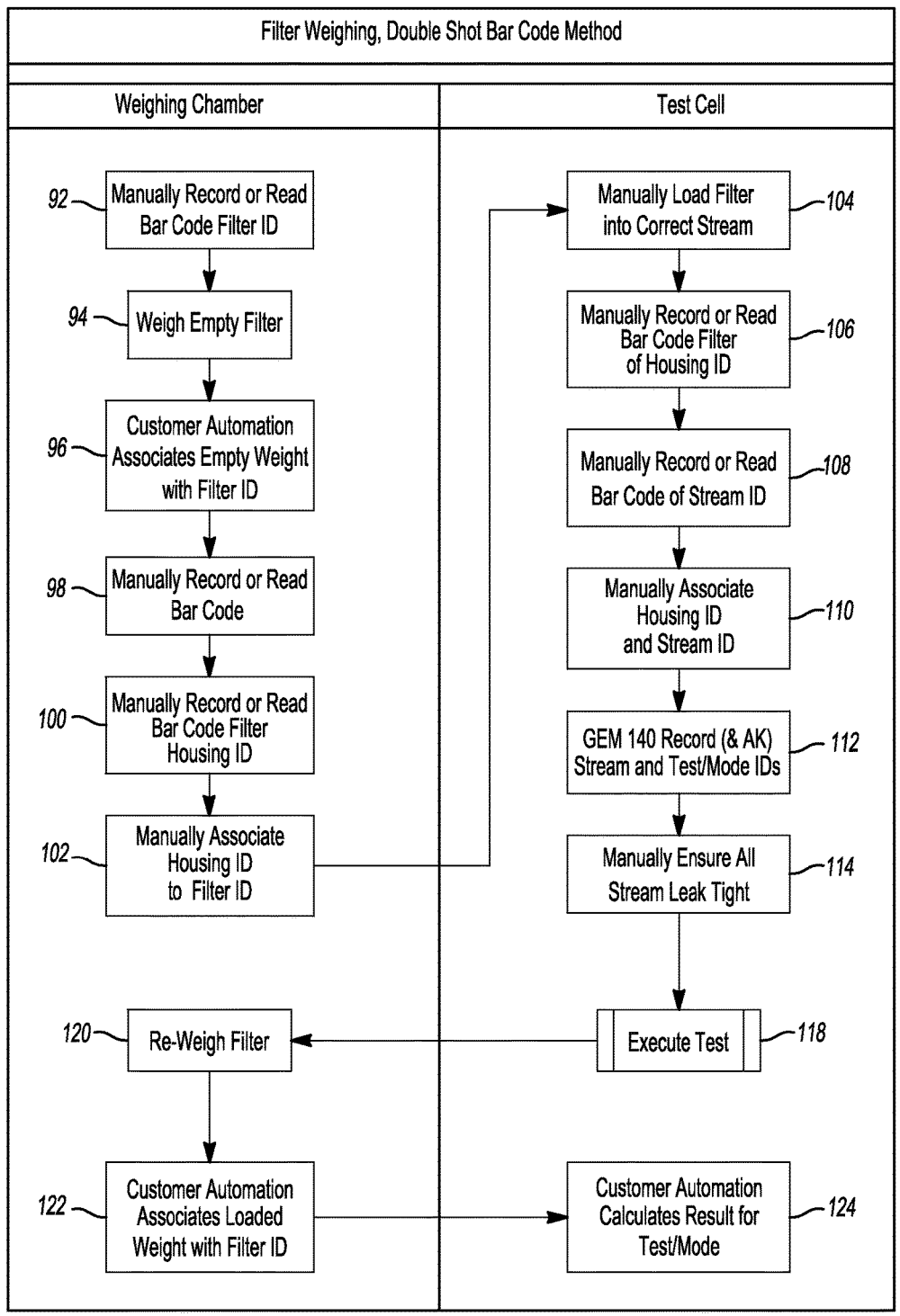
FIG. 8 is a flowchart detailing operation of an emissions measurement apparatus in accordance with the principles of the present disclosure.

With particular reference to FIG. 8, operation of the emissions test apparatus 10 will be described in detail. Once the internal combustion engine 72 is attached to the cyclone 68 and the control cabinet 70 is configured to run a particular emissions test, a filter media 14 may be manually recorded or, alternatively, may be recorded by the controller 76 by scanning the bar code 84 at 92. If the filter media 14 includes an RFID tag 100, the controller 76 may record the filter media 14 based on information provided by the RFID reader 102 when the RFID tag 100 is brought into proximity of the RFID reader 102. The filter media 14 may be brought into proximity of the RFID reader 102 manually or, alternatively, may pass by the RFID reader 102 if the filter carrier 60 is transported via automation (not shown).

Following identification of the filter media 14, the filter media 14 may be weighed at 94 to obtain a pre-test weight of the filter media 14. Once weighed, the controller 76 may assign the empty weight with a filter identification at 96 and the bar code 84 of the particular filter media 14 may once again be read and linked to the weight of the filter media 14 at 98. The filter media 14 may additionally or alternatively be linked via RFID, if present.

Following identification of the filter media 14 at 98, the filter carrier 60 associated with the filter media 14 and the filter housing 12 in which the filter media 14 is installed may also be manually identified or, alternatively, may be identified by scanning the bar codes 85, 86 respectively associated with the filter carrier 60 and the filter housing 12 at 100. After the filter housing 12 is manually identified or, alternatively, the bar codes 85, 86 are scanned, the controller 76 may associate the identification of the filter housing 12 with the identification of the filter media 14 and filter carrier 60 to link the filter media 14 and the filter carrier 60 to the particular filter housing 12 at 102. Once the controller 76 links the identification of the filter housing 12 with the particular filter media 14 and filter carrier 60, the filter media 14 and filter carrier 60 may be loaded into the filter housing 12 and the latch mechanism 36 may be moved into the latched state.

The filter media 14 and filter carrier 60 may be manually loaded into the filter housing 12. Alternatively, automation may be used to load the filter media 14 and filter carrier 60 into the filter housing 12. If automation is used to load the filter media 14 and the filter carrier 60 into the filter housing 12, the controller 76 may direct the automation to pass the filter media 14 by the RFID reader 102 to allow the RFID reader 102 to read and identify the filter media 14 via the RFID tag 100, if present.

Once the filter media 14 and filter carrier 60 are loaded into the filter housing 12 (either manually or via automation), the filter housing 12 may be fluidly coupled to the cyclone 68. Specifically, the filter housing 12—including the filter media 14 and filter carrier 60—may be fluidly coupled to the cyclone 68 and to the control cabinet 70 via the fittings 78, 80 at 104.

Once the fitting 30 of the first housing 16 is attached to the fitting 78 associated with the cyclone 68 and the fitting 48 of the second housing 18 is attached to the fitting 80 associated with the control cabinet 70, the filter housing 12 may be identified by scanning the bar code 88 at 106. Likewise, the bar code 90 associated with the fluid stream may likewise be read to identify the particular fluid stream at 108. The identification of the particular filter housing 12 and the identification of the particular fluid stream/test fixture may be associated with one another by the controller 76 at 110. At this point, identifying the filter media 14 via the bar code 84 and/or via the RFID tag 100 and identifying the filter housing 12 via the bar code 86 links the filter housing 12 to the filter media 14. Likewise, identifying the particular filter housing 12 via the bar code 88 and identifying the particular fluid stream via the bar code 90 links the particular filter housing 12 to the fluid stream. As such, the fluid stream may be linked to the filter media 14 as each of the filter media 14 and the fluid stream are linked to the particular filter housing 12. The foregoing information may be recorded and stored by the controller 76 at 112.

Once the filter media 14 is linked to the particular filter housing 12 and the particular filter housing 12 is linked to the particular fluid stream by the controller 76, the controller 76 may determine that the emissions test apparatus 10 is properly configured such that there are no leaks in the apparatus 10. The controller 76 may determine that the filter housing 12 is properly installed in the fittings 78, 80 by supplying the fitting 80 with a digital-input signal, for example. Because the fitting 80 is connected to the filter housing 12, which, in turn, is connected to the fitting 78, if the fitting 78 is at ground and the fitting 78 is properly connected to the filter housing 12 which is properly connected to the fitting 80, the controller 76 can determine that the filter housing 12 is properly connected to the fitting 78 and to the fitting 80 at 114.

While the controller 76 may check the particular fluid stream in which the filter housing 12 is installed, the test cannot be initiated until the other fluid streams of the emissions test apparatus 10 are either fluidly coupled to a filter housing 12 or, alternatively, are capped. If the emissions test apparatus 10 includes three test streams, for example, but only two filter housings 12 are under test, the third fluid stream must be capped to prevent the vacuum 74 from drawing a mixture of exhaust gas/ambient air through the cyclone 68 and into the test chamber (not shown) without drawing the mixture of exhaust gas/ambient air into a filter housing 12. Accordingly, a cap 116 (FIG. 7) may be connected to the fitting 78 if a particular fluid stream is not currently under test (i.e., if the particular fluid stream is not fluidly connected to a filter housing 12). The cap 116 may be attached to the fitting 78 in a similar manner as the fitting 30 and prevents fluid communication through the fitting 78. The cap 116 may be supplied with a digital input by the controller 76 in a similar fashion as the fitting 80 to determine whether the cap 116 is attached to the fitting 78.

Once each of the fluid streams associated with the cyclone 68 are confirmed to be connected to a cap 116 or, alternatively, are properly connected to a filter housing 12, the controller 76 may execute the emissions test at 118. As described above, the emissions test includes starting the engine 72 and causing exhaust gas to flow into the cyclone 68 where the exhaust gas is mixed with ambient air. The mixture of exhaust gas and ambient air is drawn through the fitting 78 and into the filter housing 12 via the force imparted thereon by the vacuum 74 associated with the control cabinet 70. The exhaust gas/ambient air is drawn through the filter media 14 where particulate matter disposed within the exhaust gas collects on the filter media 14.

The particular test or segment of the test may be linked to the particular filter media 14 by the controller 76. For example, if the filter media 14 is used for a portion of a test (i.e., a test segment), the particular filter media 14 may be linked to the particular test segment by scanning the bar code 84 and/or reading the RFID tag 100 and linking the particular filter media 14 to the test segment. This way, the filter media 14 can be properly attributed to a specific portion or segment of a test. While the filter media 14 is described as being linked to a test segment, the filter media 14 could be linked to the length of the entire test.

Following the test, the filter housing 12 may be disconnected from the fittings 78, 80, and the latch mechanism 36 may be moved into the unlatched state. The first housing 16 may be pivoted relative to the second housing 18 to allow removal of the filter carrier 60 and, thus, the filter media 14, from the filter housing 12. The first housing 62 may be separated from the second housing 64 and the filter media 14 may be removed from the filter carrier 60. At this point, the filter media 14 may be weighed at 120 and the weight recorded by the controller 76. The controller 76 may then associate or link the weight of the filter post-test to the filter ID at 122 and may subsequently calculate the emissions of the engine 72 at 124. As with loading of the filter media 14 and filter carrier 60, removal of the filter media 14 and filter carrier 60 may be performed manually or automatically via automation.

As described above, each of the bar codes 84, 86, 85, 88, 90 of the filter housing 12, filter media 14, filter carrier 60, and fluid stream are respectively and individually scanned and recorded by the controller 76. Additionally or alternatively, an RFID tag 100 may be scanned and identified by an RFID reader 102 to identify the filter media 14. The foregoing procedure ensures that the filter media 14 is properly associated with the filter housing 12 which, in turn, is properly associated with the fluid stream to ensure that the filter media 14 is linked to the fluid stream prior to, during, and following an emissions test. In so doing, the procedure outlined in FIG. 8 ensures that the recorded weight of the filter media 14 is attributed to the proper fluid stream and, thus, is attributed to the proper phase of the particular emissions test.

While each of the bar codes 84, 85, 86, 88, and 90 are individually scanned, the bar codes 84, 86, 88, and 90 could alternatively be scanned together. Namely, two of the bar codes may be simultaneously read by triggering a bar-code reader (not shown) a single time.

Figure 3:
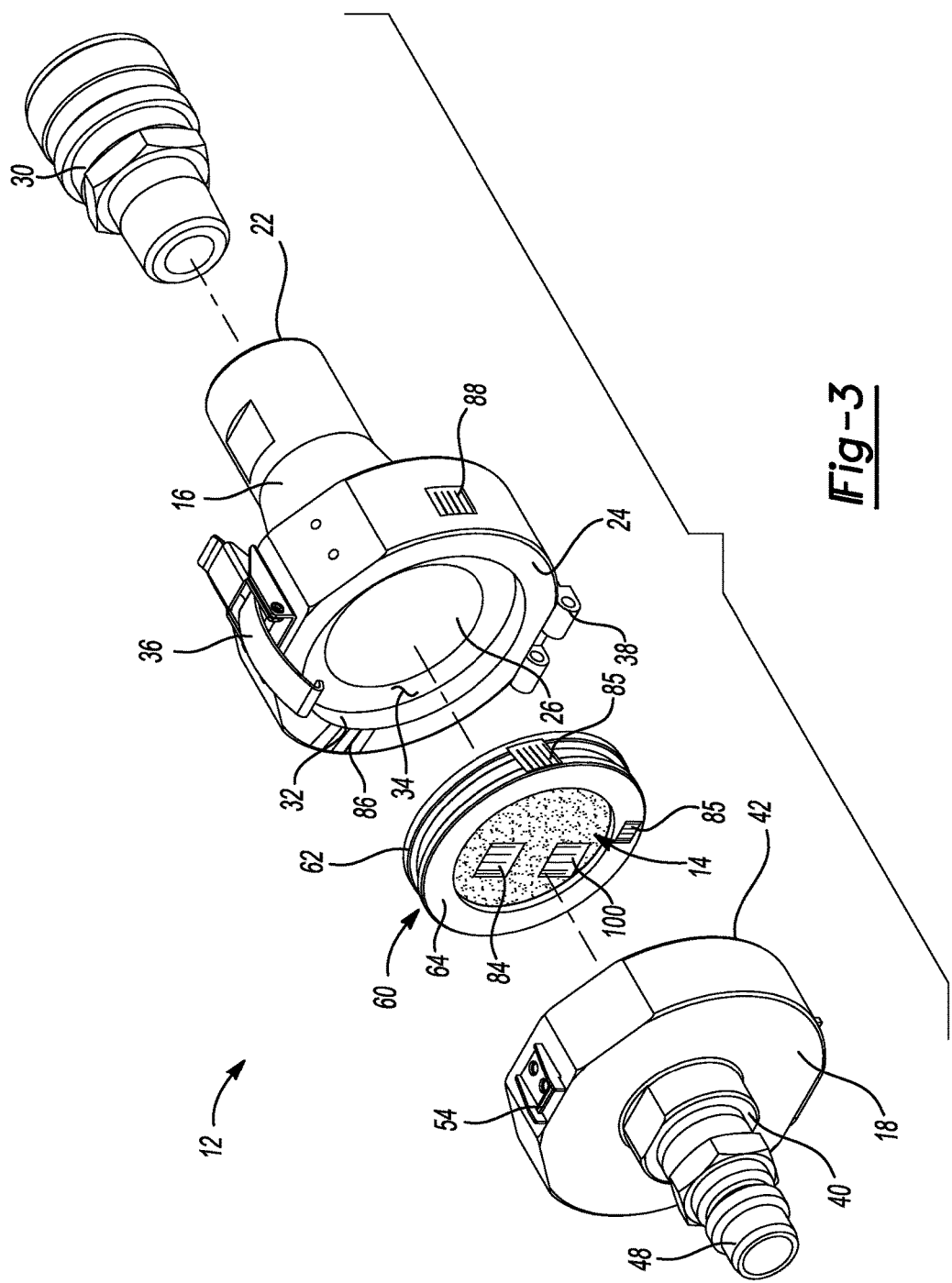
FIG. 3 is a partial exploded view of the filter housing of FIG. 1.
Figure 4:
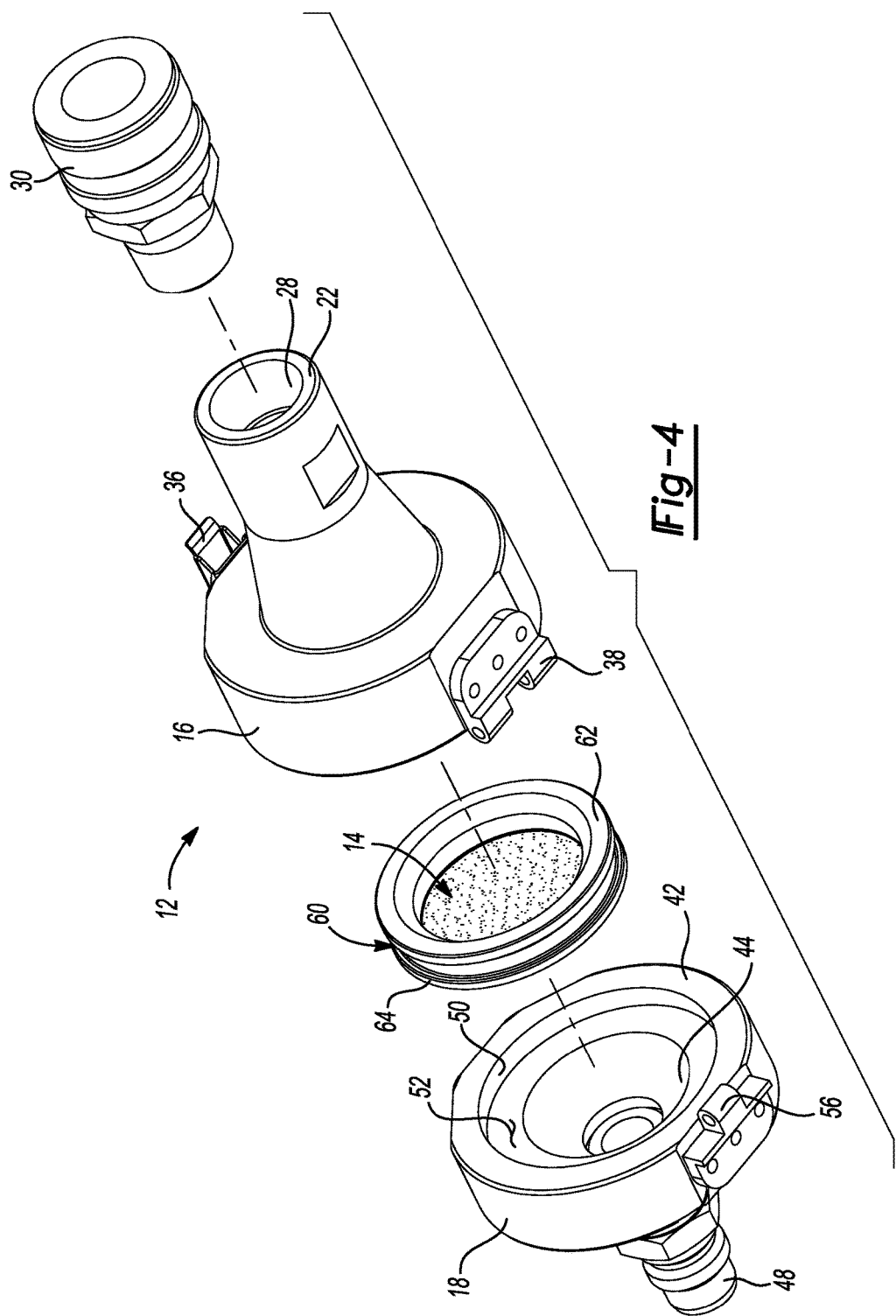
FIG. 4 is a partial exploded view of the filter housing of FIG. 1.
Figure 5:
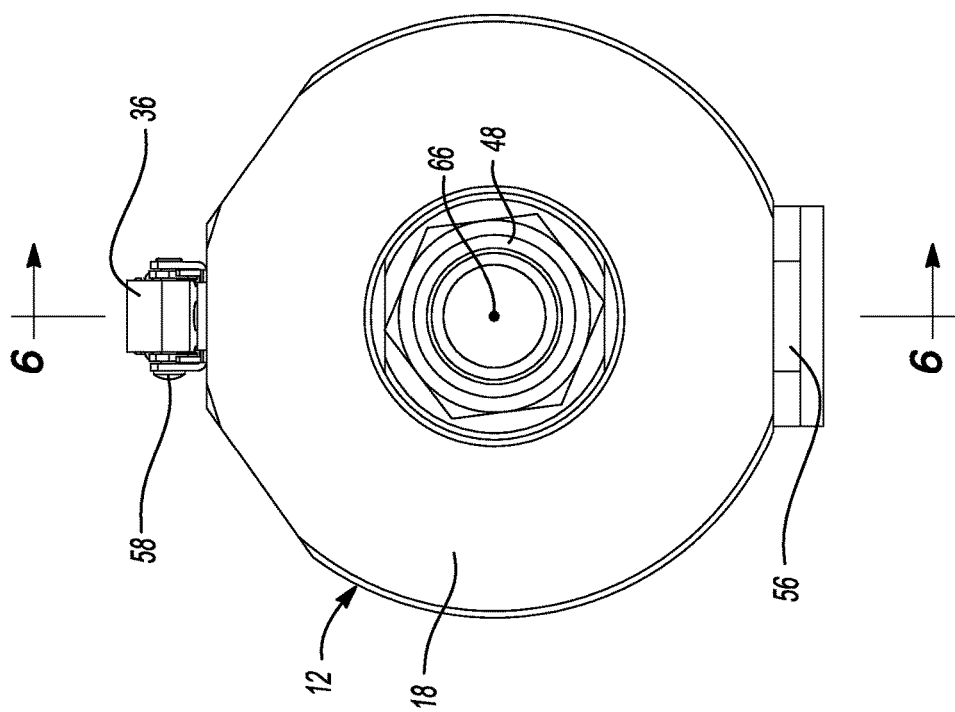
FIG. 5 is a top view of the filter housing of FIG. 1.
Figure 9A:
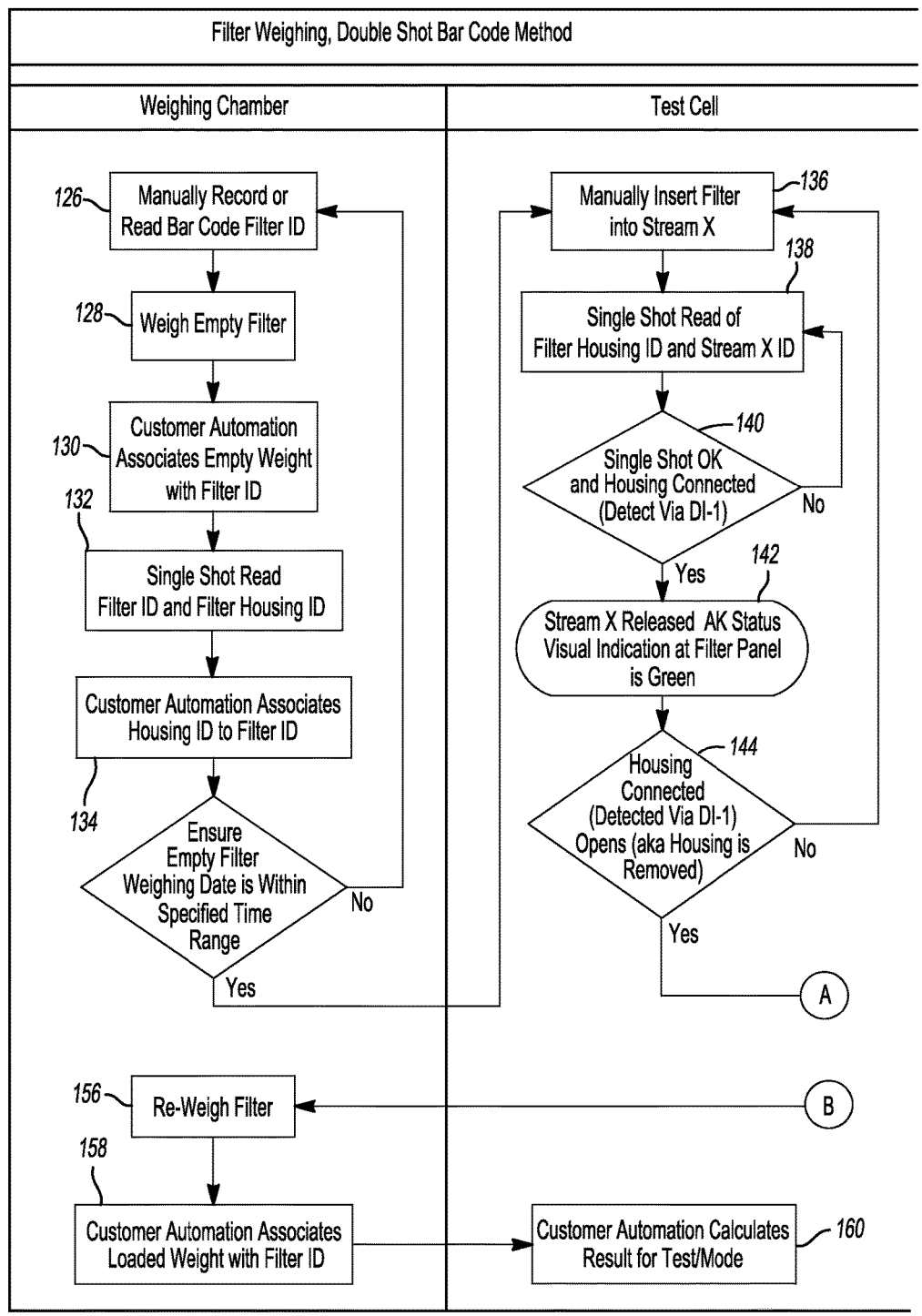
FIGS. 9A and 9B are flowcharts that detail operation of an emissions test apparatus in accordance with the principles of the present disclosure.
Figure 9B:
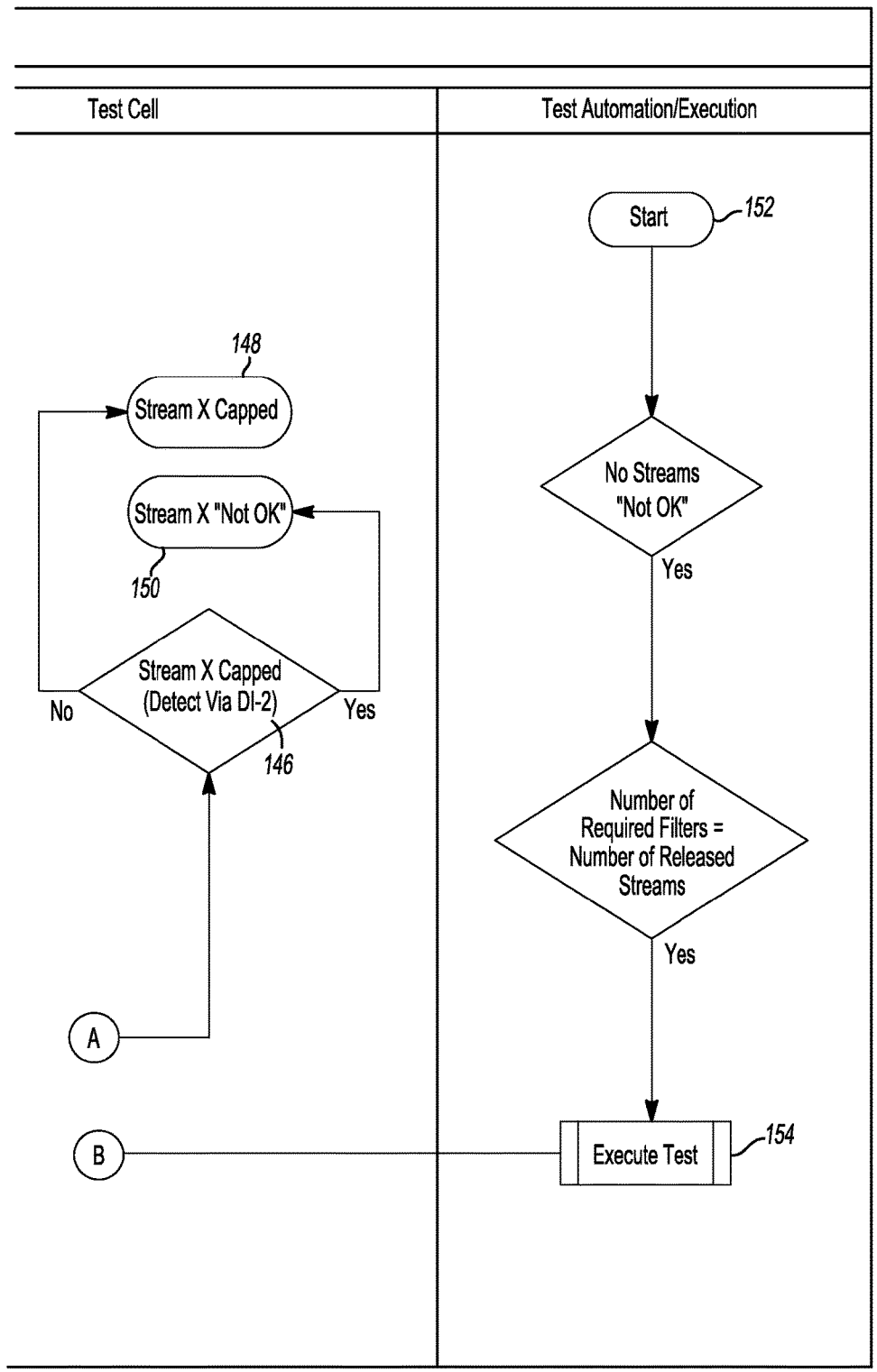

With reference to FIGS. 9A-9B, operation of the emissions test apparatus 10 will be described in detail, whereby a so-called "single shot" bar-code reader is utilized to read two bar codes simultaneously. Initially, the filter media 14 may be identified by scanning the bar code 84 associated with the filter media 14 or, alternatively, manually recording the identifier of the filter media 14 into the controller 76 at 126. The filter media 14 may be weighed at 128 with the pre-test weight being associated with the particular filter ID at 130. Once the weight of the filter media 14 is recorded by the controller 76, the bar code 84 of the filter media 14 may be simultaneously read with the bar code 86 of the filter housing 12 at 132 to automatically associate the particular filter media 14 with the particular filter housing 12 at 134. Because the bar code 84 is simultaneously read with the bar code 86, the bar code 84 may be positioned proximate to an outer diameter of the filter media 14 to allow the bar code 84 to be in close proximity to the bar code 86 associated with the first housing 16 of the filter housing 12, as shown in FIG. 3.

The controller 76 determines that the time between weighing of the empty filter at 128 and scanning of the bar codes 84, 86 is within a specified time range to ensure that the filter media 14 is not exposed to ambient air more than a predetermined time prior to being loaded into the filter housing 12 to prevent the filter media 14 from collecting particulate from the ambient air. If the time between when the filter was weighed at 128 and the time in which the filter media 14 and filter housing 12 was scanned exceeds a predetermined amount, the filter media at 114 is scanned again at 126 and is re-weighed at 128. If, on the other hand, the time between weighing of the empty filter at 128 and the time the filter housing 12 and filter media 14 are scanned is within a specified time range, the filter housing 12 may be connected to the cyclone 68 and the control cabinet 70 via the fittings 78, 80, respectively, at 136.

Once the filter housing 12 is connected to the fittings 78, 80, the bar code 88 associated with the filter housing 12 and the bar code 90 associated with the fluid stream/test fixture may be simultaneously read at 138. The controller 76 may then determine whether the filter housing 12 is properly connected to the fittings 78, 80 based on the signal supplied to the fitting 80 at 140. If the filter housing 12 is not properly connected to either or both of the fittings 78, 80, the controller 76 will not permit the bar codes 88, 90 to be read and will not allow the filter housing 12 to be linked to the particular fluid stream. If, on the other hand, the controller 76 determines that the filter housing 12 is properly connected to the fittings 78, 80, the controller 76 will identify the particular test fixture in which the filter housing 12 is installed to be ready and, therefore, will permit fluid to flow through the filter housing 12 from the cyclone 68 to the control cabinet 70 at 142.

Prior to doing so, however, the controller 76 will first check the other fluid streams to determine whether a filter housing 12 is properly installed in each fluid stream at 144. If not, the controller 76 will return to step 136 until the decision at step 144 results in each fluid stream having a filter housing 12 fluidly coupled to the cyclone 68 and to the control cabinet 70. The controller 76 will also check the other fluid streams at 146 to determine whether the fluid streams are capped (i.e., via cap 116). If the other fluid streams are capped, the controller 76 will identify the capped stream at 148 or, alternatively, will identify the fluid stream as uncapped at 150. If each fluid stream is properly connected to a filter housing 12 or, alternatively, the other fluid streams are properly capped, the controller 76 will proceed to start the particular emissions test at 152.

The controller 76 will proceed to execute the test at 154, thereby drawing a mixture of exhaust gas and ambient air through the filter media 14. Following the test, the filter media 14 will be removed from the filter housing 12, as described above, and the filter media 14 will be re-weighed at 156. The post-weight of the filter will be recorded at 158 and once again the bar code 84 of the filter media 14 will be scanned to link the post-test weight of the filter media 14 to the particular filter media 14 at 158 and, subsequently, the emissions of the internal combustion engine 72 will be calculated at 160.

In each of the foregoing emissions tests (FIGS. 8, 9A, and 9B), the filter media 14 is identified and linked to the particular filter housing 12 in which the filter media 14 is disposed and, further, may be linked to a particular filter carrier 60. Subsequently, the particular filter housing 12 is linked to the particular test fixture/fluid stream to link the filter housing 12 to the particular test fixture/fluid stream. Accordingly, the test fixture/fluid stream is linked to the filter media 14, thereby ensuring that the post-test weight of the filter media 14 is properly linked to the filter housing 12 and to the fluid stream. As a result, the weight of the filter media 14 is properly attributed to the correct phase of the emissions test, thereby resulting in an accurate calculation of the emissions of the internal combustion engine 72.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An emissions test apparatus comprising:
 a filter housing having at least one of a first RFID tag, a first bar code, and a third bar code identifying said filter housing, said filter housing including a first fitting disposed at a first end and a second fitting disposed at a second end, wherein said first fitting and said second fitting are configured to connect said filter housing to a test fixture;
 a filter media selectively disposed within said filter housing and including at least one of a second RFID tag and a second bar code identifying said filter media, wherein said test fixture includes a fourth bar code identifying a fluid stream; and
 a controller operable to:

link said filter housing and said filter media when said filter media is disposed within said filter housing based on information provided by said at least one of said first RFID tag and said first bar code and said at least one of said second RFID tag and said second bar code; and link said filter housing to said test fixture based on information provided by (i) said at least one of said first RFID tag, said first bar code, and said third bar code and (ii) said fourth bar code.

2. The emissions test apparatus of claim 1, wherein said first bar code and said second bar code are disposed a predetermined distance from one another to allow simultaneous reading of said first bar code and said second bar code.

3. The emissions test apparatus of claim 1, wherein said third bar code and said fourth bar code are disposed a predetermined distance from one another to allow simultaneous reading of said third bar code and said fourth bar code.

4. The emissions test apparatus of claim 1, wherein said controller is operable to link said filter housing to said test fixture based on information provided by said third bar code and said fourth bar code.

5. The emissions test apparatus of claim 4, wherein said controller is operable to link said filter media to said test fixture based on information provided by said at least one of said first RFID tag and said first bar code, said at least one of said second RFID tag and second bar code, said third bar code, and said fourth bar code.

6. The emissions test apparatus of claim 1, wherein said controller is operable to determine whether said first fitting and said second fitting are installed in said test fixture.

7. The emissions test apparatus of claim 6, wherein said controller prevents reading of said third bar code and said fourth bar code unless said first fitting and said second fitting are installed in said test fixture.

8. The emissions test apparatus of claim 6, wherein one of said first fitting and said second fitting is supplied with an input to allow said controller to determine if said first fitting and said second fitting are connected to said test fixture.

9. The emissions test apparatus of claim 1, wherein said test fixture is configured to expose said filter housing and said filter media to a stream of exhaust gas produced by an engine.

10. The emissions test apparatus of claim 1, wherein said third bar code is different than said first bar code.

11. An emissions test apparatus comprising:
a filter housing having at least one of a first RFID tag and a first bar code identifying said filter housing;
a filter media selectively disposed within said filter housing and including a second RFID tag identifying said filter media;
a controller operable to link said filter housing and said filter media when said filter media is disposed within said filter housing based on information provided by said first RFID tag and said second RFID tag; and
a test fixture connected to said filter housing to selectively expose said filter housing and said filter media to a stream of exhaust gas produced by an engine, said test fixture including a second bar code identifying said exhaust stream, wherein said controller is operable to link said filter housing to said test fixture based on information provided by (i) said at least one of said first RFID tag and said first bar code and (ii) said second bar code.

12. The emissions test apparatus of claim 11, wherein said controller is operable to link said filter housing to said test fixture based on information provided by said first bar code and said second bar code.

13. The emissions test apparatus of claim 12, wherein said controller is operable to link said filter media to said test fixture based on information provided by said first bar code, said second bar code, said first RFID tag, and said second RFID tag.

14. The emissions test apparatus of claim 11, wherein said filter housing includes a first fitting disposed at a first end and a second fitting disposed at a second end, wherein said first fitting and said second fitting are configured to connect said filter housing to said test fixture.

15. An emissions test apparatus comprising:
a filter carrier having at least one of a first RFID tag and a first bar code identifying said filter carrier;
a filter media selectively disposed within said filter carrier and including a second RFID tag identifying said filter media;
a controller operable to link said filter carrier and said filter media when said filter media is disposed within said filter carrier based on information provided by said first RFID tag and said second RFID tag; and
a test fixture connected to said filter carrier to selectively expose said filter carrier and said filter media to a stream of exhaust gas produced by an engine, said test fixture including a second bar code identifying said exhaust stream, wherein said controller is operable to link said filter carrier to said test fixture based on information provided by (i) said at least one of said first RFID tag and said first bar code and (ii) said second bar code.

16. The emissions test apparatus of claim 15, wherein said controller is operable to link said filter carrier to said test fixture based on information provided by said first bar code and said second bar code.

17. The emissions test apparatus of claim 16, wherein said controller is operable to link said filter media to said test fixture based on information provided by said first bar code, said second bar code, said first RFID tag, and said second RFID tag.

18. The emissions test apparatus of claim 15, further comprising a filter housing configured to hold said filter media, said filter housing including a first fitting disposed at a first end and a second fitting disposed at a second end, wherein said first fitting and said second fitting are configured to connect said filter housing to said test fixture.

19. An emissions test apparatus comprising:
a filter carrier having at least one of a first RFID tag and a first bar code identifying said filter carrier;
a filter media selectively disposed within said filter carrier and including at least one of a second RFID tag and a second bar code identifying said filter media;
a controller operable to link said filter carrier and said filter media when said filter media is disposed within said filter carrier based on information provided by said at least one of said first RFID tag and said first bar code and said at least one of said second RFID tag and said second bar code; and
a test fixture connected to said filter carrier to selectively expose said filter carrier and said filter media to a stream of exhaust gas produced by an engine, said test fixture including a third bar code identifying said exhaust stream, wherein said controller is operable to link said filter carrier to said test fixture based on information provided by (ii) said at least one of said first RFID tag and said first bar code and (ii) said third bar code.

20. The emissions test apparatus of claim 19, wherein said controller is operable to link said filter media to said test fixture based on information provided by said at least one of said first RFID tag and saki first bar code, said at least one of said second RFID tag and second bar code, and said third bar code.

21. The emissions test apparatus of claim 19, further comprising a filter housing configured to hold said filter media, said filter housing including a first fitting disposed at a first end and a second fitting disposed at a second end, wherein said first fitting and said second fitting are configured to connect said filter housing to said test fixture.

* * * * *

UNITED STATES PATENT AND TRADEMARK OFFICE
CERTIFICATE OF CORRECTION

| | | |
|---|---|---|
| PATENT NO. | : 9,829,413 B2 | Page 1 of 1 |
| APPLICATION NO. | : 14/410417 | |
| DATED | : November 28, 2017 | |
| INVENTOR(S) | : Gerald Marek et al. | |

It is certified that error appears in the above-identified patent and that said Letters Patent is hereby corrected as shown below:

Column 15, Line 1 (Claim 19):
Delete "(ii)" and insert --(i)--

Column 15, Line 7 (Claim 20):
Delete "saki" and insert --said--

Signed and Sealed this
Thirteenth Day of March, 2018

Andrei Iancu
*Director of the United States Patent and Trademark Office*